United States Patent [19]

Wijnendaele

[11] 4,314,993

[45] Feb. 9, 1982

[54] IMMUNOGENIC E. COLI ST ENTEROTOXIN DERIVATIVES AND COMPOSITIONS CONTAINING THEM

[75] Inventor: Frans V. Wijnendaele, Ottenburg, Belgium

[73] Assignee: Smithkline-RIT, Belgium

[21] Appl. No.: 137,326

[22] Filed: Apr. 4, 1980

[51] Int. Cl.³ .................. A61K 39/108; A61K 39/02; C07G 7/00
[52] U.S. Cl. ........................... 424/92; 424/177; 424/88; 260/112 R
[58] Field of Search ............... 424/87, 88, 92, 91; 260/112 R

[56] References Cited

U.S. PATENT DOCUMENTS

| | | | |
|---|---|---|---|
| 3,761,585 | 9/1973 | Mullan | 424/91 |
| 3,794,630 | 2/1974 | Mullan | 260/112 R |
| 4,180,562 | 12/1979 | Patterson | 424/91 |
| 4,220,584 | 9/1980 | Xenyuco et al. | 424/92 |
| 4,237,115 | 12/1980 | Brinton Jr. | 424/92 |

FOREIGN PATENT DOCUMENTS 1452648  10/1975  United Kingdom.

OTHER PUBLICATIONS

Gyles et al., J. Infect. Dis., vol. 1203 p. 419 (1969).
Smith et al., J. Med. Microbiol., vol. 3, p. 387 (1970).
Giannella, Infect. Immun., vol. 14, p. 95 (1976).
Hughes et al., Nature, 271: 755 (1978).
Alderete et al., Infect. Immun., 19:1021 (1978).
Kapitany et al., Infect. Immun., 26:173 (1979).
Evans et al., Infect. Immun., 8:731 (1973).
Alderete et al., Infect. Immun., 15:781 (1977).
Bachmann,Bacteriol. Rev., 36(4):525 (1972).
Rappaport et al., Infect. Immun., 9(2):304 (1974).
Desormeau-Bedot et al., Bull. Acad. Vet. Fr., 49(4):445 (1976).
Kech et al., Eur. J. Immunol., 3(2)99; (1973).
Kech, J. Immunol. Meth., 20:287 (1978).
Avrameas et al., Immunochem., 6:53 (1969).
Lee et al., Am. Soc. of Microbiology 1973 Meeting, Abst. No. M168.
Fallier et al., Am. Soc. of Microbiology 1979 Meeting, Abst. No. B34.
Madsen et al., American Society of Microbiology 1979 Meeting, Abst. No. P29.
Uy and Wold, Advances in Experimental Medicine and Biology, Chapter 9, pp. 169-186.
Takeda et al., Infect. Immun., 25:978 (1979).
Dean, J. Infect. Dis., 125:407 (1972).

*Primary Examiner*—Blondel Hazel
*Attorney, Agent, or Firm*—Janice E. Williams; Richard D. Foggio; Alan D. Lourie

[57] ABSTRACT

*E. coli* heat stable (ST) enterotoxin derivatives are prepared by reaction of *E. coli* ST enterotoxin with crosslinking agents for proteins. The so-obtained crosslinked ST enterotoxins show immunogenic activity; they are valuable prophylactic agent for protecting man and animals against diarrheal disease provoked by *E. coli* enterotoxin and they may be formulated into compositions for intramuscular, subcutaneous or oral administration.

2 Claims, No Drawings

IMMUNOGENIC E. COLI ST ENTEROTOXIN DERIVATIVES AND COMPOSITIONS CONTAINING THEM

The present invention relates to novel immunogenic E. coli heat stable enterotoxin derivatives, to the method of production thereof and to prophylactic antidiarrheal compositions containing said immunogenic E. coli heat stable enterotoxin derivatives for administration to man and animals.

It is known that Escherichia coli strains may be responsible for diarrheal disease in man as well as in animals and, from different studies (e.g. Gyles and Barnum J. Infect. Dis. 120, 419–426, 1969), it has been shown that enteropathogenicity of E. coli strain is related to the production of enterotoxins.

Two enterotoxins have been described: a heat-labile (LT) enterotoxin and a heat-stable (ST) enterotoxin and Smith and Gyles (J. Med. Microbiol. 3, 387–401, 1970) have classified a certain number of enteropathogenic E. coli strains of different animal origins as producers of either LT and ST enterotoxins or of ST enterotoxin only. ST producer E. coli strains of human origin have also been described or referred to by different authors (e.g. R. A. Giannella, Infect. Immun. 14, 95–99, 1976). The heat-labile enterotoxin is under the genetic control of a transmissible plasmid; it appears to consist of a group of linked peptides with a molecular weight of about 24,000. The LT enterotoxin is adsorbed to gangliosides at the brush border of epithelial cells of the small intestine where, through mediation of an enzymatic process, it causes hypersecretion of water and chlorides into the gut lumen and inhibits reabsorption of sodium so that the gut lumen becomes distended with fluid involving hypermotility and diarrhea. The LT enterotoxin is antigenic and stimulates neutralizing antibodies in the serum of persons or animals who have been previously infected with toxin-producer strains of E. coli. The heat-stable enterotoxin is under the genetic control of a heterogeneous group of plasmids; it also causes diarrhea, perhaps by stimulating guanidine cyclase (J. M. Hughes et al., Nature 271, 755–6, 1978). Considering that antiserum prepared against organisms that produce LT and ST was shown to neutralize LT but not ST and that antisera prepared in a similar way against ST had no neutralizing effect on ST or on LT, Smith and Gyles (loc. cit.) concluded that ST is not antigenic. In a paper entitled "Purification and Chemical Characterization of the Heat-Stable Enterotoxin Produced by Porcine Strains of Enterotoxygenic Escherichia coli" (Infect. Immun. 19, 1021–1030, 1978) J. F. Alderete and D. C. Robertson reported that purified ST "exhibited a molecular weight of 4,400, as determined by both sodium dodecyl sulphate-gel electrophoresis and gel filtration" and that "a molecular weight of 5,100, representing 47 residues, was calculated from amino acid analysis data"; they also indicate that "antiserum obtained from rabbits immunized with ST or ST coupled to bovine serum albumin neutralized the action of the enterotoxin in suckling mice; however, passive hemagglutination and hemolysis titer assays suggested that ST is a poor antigen." ST molecular weight determination by other authors led to different and lower values (e.g. 1,000–1,200, 1,500–2,000 and 2,500 daltons as indicated by E. V. Lee et al., R. Lallier et al. and G. L. Madsen et al. in American Society of Microbiology meeting, 1973 abstract M168, 1979 abstract B34 and 1979 abstract P29 respectively), these discrepancies being possibly due to differences in the ST production, isolation or purification step as well as different enzymatic processings when the enterotoxin is leaving the cell.

Recent studies (R. A. Kapitany et al., Infect. Immun. 26, 173–177, 1979) reach the question of the heterogenicity of ST but the finding of different types of ST based—as indicated by R. A. Kapitany et al. (loc. cit.)—on amino acid composition, heat stability properties and biological activity is without any incidence on the present invention which is indistinctly applicable to each amino acids composition of the different ST enterotoxins.

Various media and incubation methods have been used by different investigators in the culture of different E. coli ST producer strains. Examples of such media are the complex medium of F. G. Evans et al. (Infect. Immun. 8, 731–35, 1973), and the minimal defined medium of J. F. Alderete et al. (Infect. Immun. 15, 781–88, 1977) and modifications thereof.

In the following examples, the ST enterotoxin is prepared from a porcine E. coli strain K12 which has been deposited on Mar. 13, 1980 with the American Type Culture Collection (Rockville, Md., USA) under accession number ATCC 31621.

E. coli strain ATCC 31621 is a mutant strain derived from the well known E. coli K12 strain isolated from the stool of a convalescent diphteria patient in 1922 and universally used for fundamental research in bacterial genetics and molecular biology (B. J. Bachmann, Bacteriol. Rev. 36, 4, 525, 1972). E. coli K12 is a rod-shaped gram-negative bacteria, about two microns in length and one micron in diameter. Growth occurs best at 37° C. but the strain also grows and divides at temperatures as low as 20° C. E. coli K12 is a noncapsulated motile bacteria with $O^-:K$ (?):H 48 serotype; it shows a very specific sensitivity towards the lambda phage.

The E. coli strain ATCC 31621 shows the above typical characteristics of E. coli K12 and, moreover, it has auxotrophic requirements for phenylalanine, tryptophan, histidine and proline and does not ferment lactose, probably due to a lac y mutation (it forms white colonies on Mc Conkey's lactose medium). The E. coli strain ATCC 31621 harbours a recombinant plasmid with a $2.1 \times 10^6$ daltons DNA fragment obtained by restriction endonuclease digestion of a plasmid DNA originally derived from a pathogenic porcine strain of E. coli and carrying a gene coding for the synthesis of heat stable enterotoxin. The strain is chloramphenicol resistant (25 mcg per ml).

As indicated above, the invention is not restricted to the use of either the E. coli strain ATCC 31621 or to the hereinafter described fermentation process, said strain and fermentation conditions being purely exemplative for the production of ST enterotoxin.

According to the present invention, there is provided a process for the preparation of ST enterotoxin derivatives, which process comprises the reaction of ST enterotoxin with a bifunctional crosslinking agent for proteins and the so-obtained ST enterotoxin derivatives are thus inter- or intramolecularly crosslinked ST enterotoxin showing substantially higher molecular weight than ST enterotoxin itself.

In the process of the present invention, ST enterotoxin is allowed to react with a non-toxic bifunctional crosslinking agent for proteins acting either as a homofunctional or as a heterofunctional reagent to yield a crosslinked ST enterotoxin, examples of bifunctional protein crosslinking agents acting as homofunctional reagents are di-aldehydes; di-ketones; carbodiimides; diisocyanates; diisothiocyanates; aryldiazides; acyldiazides; aryl (activated) difluorides; aryl disulfonyl (activated) chlorides or bromides; dicarboxylic acid (activated) azides, chlorides or esters; di-alpha haloketones; polymethylene (n=3-12) diimidic acid esters; bis-(maleidomethyl) ethers; gem-bis-diazoacetyl alkanes; bis-diazoarene and N,N'-arylene-dimaleimides and examples of heterofunctional reagents are those presenting two different but compatible functional groups of the hereinabove crosslinking agents, more particularly isocyanato- and isothiocyanato-arenes; (activated) fluoro- and azido-arenes; (activated) azido- and fluoro-arenes; (activated) azido-aryl alpha-haloalkyl ketones; chloro- or bromo-acetimidic acid lower alkyl esters; chloroformic acid lower alkyl esters and epihalohydrins.

The bifunctional crosslinking agents for proteins herein referred to are well known in the art. For instance, a review of artificial crosslinks into proteins has been published by Rosa UY and Finn WOLD in chap. 9 of Advances in Experimental Medicine and Biology entitled Protein Crosslinking (Biochemical and Molecular Aspects) edited by Mendel Friedman, Plenum Press, New York.

Among these different crosslinking agents, the most commonly used for practical reasons are homofunctional reagents such as glutaraldehyde, difluorodinitrobenzene, the isocyanate and isothiocyanate compounds, the carbodiimides and the diimidic acid esters.

Thus, according to the present invention, there is provided a process for the preparation of *E. coli* ST enterotoxin derivatives, which process comprises the reaction of ST enterotoxin with a protein crosslinking agent.

The *E. coli* ST enterotoxin employed as starting material in the process of this invention may be obtained from any *E. coli* ST enterotoxin producer strain.

The obtained ST enterotoxin present in the culture supernatant is then usually extracted and purified by removing some of the contaminants e.g. by ultrafiltration, gel filtration chromatography, ion exchange chromatography, extraction with ethanol or polyacrylamide gel disc electrophoresis. A description of some of these techniques can be found in a paper published by Y. Takeda et al. in Infect. Immun. 25, 978-985, 1979.

Since the ST enterotoxin is fairly resistant to temperature, the process of this invention can take place over a wide range of temperatures although in practice it is preferred to operate at a temperature below 37° C. and more particularly at room temperature, i.e. about 20°-25° C.

The reaction takes place in aqueous and preferably buffered medium, at a pH depending on the nature of the crosslinking agent: for instance, in the case of di-aldehydes or di-ketones the pH of the reaction is not critical and a suitable pH ranges from about 4 to about 8, a pH of about 5 being preferred and very low pH values being avoided in order to reduce possible self condensation of the aldehyde. A pH of 5 is also suitable for the carbodiimide and isocyanate crosslinking agents but for the epihalohydrin, a slightly alkaline pH (e.g. about pH 8) is suitable.

When a dialdehyde or a diketone is used for crosslinking ST enterotoxin present in low concentration in the medium, the crosslinking reaction can be improved by precipitating the ST by salting out technique—e.g. by addition of sodium sulfate—before adding thereto the crosslinking reagent.

The solubility of the obtained ST enterotoxin derivative is influenced by the different possible degrees of crosslinking.

The ST enterotoxin derivatives of the invention may be formulated into pharmaceutical or veterinary preparations for intramuscular or oral administration by addition of an acceptable carrier for such administration. Suitable carriers include isotonic salt or buffer solutions and other materials well known in the art.

According to the aqueous solubility of the ST enterotoxin derivative, the administered pharmaceutical or veterinary composition may be either a solution or a suspension, nevertheless an adjuvant such as Freund complete adjuvant (for veterinary use), aluminium hydroxide or the like may be included and, in practice, the composition will be stored in freeze-dried form and the solution (or suspension) will be reconstituted extemporaneously, e.g. by addition of Freund complete adjuvant. A dosage unit of ST enterotoxin derivative according to the invention will contain for instance 0.1 mg of crosslinked ST per kg of body weight.

The ST enterotoxin derivatives of the invention may also serve other purposes, e.g. for the easy preparation of anti ST antisera useful for immunoassay.

EXAMPLE 1

*E. coli* strain ATCC 31621 is re-hydrated with sterile saline and incubated for 18 hours at 37° C. in Petri dishes containing each 20 ml of Selective LB agar solid medium (a product manufactured and sold by DIFCO Laboratories, Detroit 1, Mich. USA) supplemented with 25 mcg of chloramphenicol per ml and previously heated for 45 minutes at 115° C.

A liquid culture medium (named PP3) is then prepared by dissolving Proteose peptone N° 3 (a product manufactured and sold by DIFCO Laboratories) 30 g, yeast extract (4 g) and dextrose (5 g) in one liter of water at 60° C. After cooling, NaCl (5 g), $Na_2HPO_4$ (5.05 g) and $KH_2PO_4$ (1.2 g) are added thereto. The medium, the pH of which is 6.9-7.0 is filtered on Seitz EKS filter and 30 ml aliquots are distributed into 250 ml culture flasks.

These culture flasks are inoculated with the smooth colonies obtained on Petri dishes, using four colonies per 30 ml of PP3 liquid medium and incubated for seven hours at 37° C. with shaking on rocking shelves (20 to 30 rockings per minute).

A second passage (for a 16 hour period) is then performed in 800 ml of PP3 medium contained in a 6 l conical flask using a 5% (v/v) inoculum of the first passage.

The obtained preculture is used as inoculum (5% v/v) for the production step carried out in fermentor vessel containing 80 l of modified Alderete medium ($K_2HPO_4$, 8.71 g; NaCl, 2.35 g; $NH_4Cl$, 1.0 g; tricine 1.8 g; $MgSO_4$.7 aq, 50 mg; $MnCl_2$.4 aq, 4.95 mg and $FeCl_3$, 4.9 mg in one liter of water) sterilized for 30 minutes at 121° C. and thereafter supplemented with l-proline, 1.42 g; l-aspartic acid 0.87 g: l-alanine 0.39 g; l-serine 0.69 g; l-phenylalanine 0.05 g: l-histidine 0.05 g; l-tryptophane 0.05 g and 5 g of Casamino Acids (a product manufactured and sold by DIFCO Laboratories, Detroit 1, Mich., U.S.A.) for one liter of final solution, the amino acids ingredients being separately prepared as 10 times concentrated solution, adjusted to pH 7.5 and sterilized for 30 minutes at 121° C. before being incorporated to the initial solution.

The production medium is incubated aerobically with stirring at 36° C. for a ten to 15 hour period, i.e. when the pH reaches 8.2–8.4 and when the oxygen consumption is approaching zero.

At the end of the production step the broth is brought to 60° C. for 30 minutes and centrifuged at 6000 g and the supernatant is filtered on Seitz EKS1 filter.

ST enterotoxin is then concentrated and purified by a 3 steps process, as follows:

In the first step, a 40 liters aliquot of filtered fermentation medium is concentrated up to a 5 liters volume by filtration on Pellicon PTAC membrane having a cut-off of 1,000 (Pellicon PTAC is the trademark of a cellulose mixed esters ultra membrane manufactured and sold by Millipore Corporation, Bedford, Mass., USA) followed by dialysis on the same Pellicon PTAC membrane until the conductivity has decreased to 500 microsiemens. The retained fraction is then further concentrated up to one liter and lyophilized. The freeze-dried product is called ST-MP.

In the second step a 3 grams aliquot of ST-MP product is dissolved in 150 ml of water and the solution is cooled to 0°–4° C. Cold acetone (1.5 liter) is added dropwise with stirring which is maintained for 30 minutes after complete addition of the acetone. The mixture is centrifuged at 3000 g and the supernatant is concentrated under reduced pressure up to a 30 ml volume to which there is added 180 ml of a methanol/chloroform 2:1 (v/v) mixture. After vigorous shaking, 42 ml of water is added and the upper layer is separated, evaporated to dryness under reduced pressure and freeze-dried. The freeze-dried product is herein referred to as ST-ACF-D.

In the third step, a 200 mg aliquot of ST-ACF-D is dissolved in two ml of water and applied to the top of a refrigerated column (2.5×30 cm) containing 50 g of Servachrom-8 (Servachrom-8 is the trademark of a chromatographic grade polyacrylic methyl ester solid by SERVA G.m.b.H. and Co. Heidelberg, German Federal Republic) equilibrated with water. Elution is performed with water. After elution of a first fraction, elution is continued with a methanol/water 6:4 (v/v) mixture to eluate the ST-containing fraction. ST is isolated by evaporation of the solvent and the obtained residue is named ST-PAE.

ST-PAE shows a 1,000–4,000 purification factor versus the initial batch activity, the specific activity of the ST-PAE product varying between 5.5 and 15 nanograms from batch to batch.

The biological activity of the fractions is determined by the infant mice test according to the method described by A. G. Dean (J. Infect. Dis. 125, 407–411, 1972). Therefore, 48–72 hours old baby mice are inoculated intragastrically with 0.025 ml of toxin solution and the accumulation of liquid in the intestine is measured two hours later. The gut weight/body weight ratio is a measure of the biological activity of the toxin. Values higher than or equal to 0.09 are considered as positive. The specific activity of a ST fraction is then expressed as the amount of ST (in nanograms of lyophilized product) which gives a gut weight/body weight value of 0.100 in the infant mice test.

EXAMPLE 2

ST-PAE (10 mg) is dissolved in 0.25 ml of acetate buffer (pH 5.1) and precipitated therefrom by addition of 0.25 ml of a 36% solution (w/v) of sodium sulfate in the same buffer. Aqueous glutaraldehyde (20 microliters of a 25% v/v solution) is added thereto and the reaction is allowed to proceed for two hours at room temperature. After that reaction time the excess reagent is separated by centrifugation and washing with water and the precipitate is freeze-dried.

The freeze-dried product consists in immunogenic crosslinked ST of increased molecular weight versus the unmodified ST used as starting material as determined by gel chromatography on Sephadex G-100 (Sephadex is the trademark of a chromatography grade dextran preparation manufactured and sold by Pharmacia, Uppsala, Sweden).

For demonstrating the molecular weight increase, the freeze-dried product is partially solubilized by adding one ml of water and with stirring the mixture for two hours at room temperature. The solubilized fraction represents from 30 to 50% of the insoluble fraction and shows a main peak at 10,000 while in the same conditions the starting ST-PAE material shows a main peak at 4000 (peak behind Vt on Sephadex G-100, Vt being the bed-volume of the column).

EXAMPLE 3

ST-PAE (20 mg) is dissolved in one ml of water and a solution of 200 mg of 1-ethyl-3(3-dimethylaminopropyl)carbodiimide hydrochloride is added thereto. The mixture is allowed to stand at 25° C. for 12 hours during which crosslinking reaction proceeds. The soluble reaction product is dialyzed on PM-10 Amicon membrane (Amicon is the trademark of an ultramembrane manufactured and sold by Amicon Corporation, Lexington, Mass., USA) to remove unreacted ST and the retained fraction (13 mg) is freeze-dried. The molecular weight of this crosslinked ST is about 10,000 (versus 2,000 for the starting material) when determined by gel chromatography on Sephadex G-100 as indicated in example 2. Also the absorption spectrum of this crosslinked ST is different from the absorption spectrum of the ST-PAE fraction employed as starting material.

EXAMPLE 4

ST-PAE (5 mg) is dissolved in 0.5 ml of 0.1 M borate ($Na_2B_4O_7$/NaOH) buffer pH 8.0 and 100 microliters of 0.02 M difluorodinitrobenzene in ethanol is added thereto. The crosslinking reaction is allowed to proceed under stirring for 4 hours at room temperature. After that reaction time the unreacted ST is discarded by dialysis through a Spectrapor dialysis tubing having a cut off of 14,000 (Spectrapor is the trademark of a dialysis tubing manufactured and sold by Spectrum Medical Industrie, New York, USA).

By gel chromatography on Sephadex G-100 (as indicated in example 2) the molecular weight of this soluble crosslinked ST is estimated to 50,000 (versus 2,000 for the starting ST-PAE). The absorption spectrum of the obtained crosslinked ST also shows an additional peak at 350 nanometers versus the absorption spectrum of the starting ST-PAE.

EXAMPLE 5

Freeze-dried ST enterotoxin derivative (100 mg) as obtained at the end of example 2 is suspended in 0.5 liter of physiological saline and 0.5 liter of Freund complete adjuvant and the composition is distributed into glass vials containing each one effective dose of crosslinked ST enterotoxin for veterinary administration. The vials are then tightly closed and kept at 4° C.

EXAMPLE 6

Freeze-dried ST enterotoxin derivative (100 mg) as obtained at the end of example 2 is suspended in one liter of physiological saline and 10 g of Alhydrogel (a product manufactured and sold by Superfos Export Company, Copenhagen, Denmark) and the composition is distributed into glass vials, each containing one effective dose of crosslinked ST enterotoxin for human administration. The vials are then tightly closed and kept at 4° C.

EXAMPLE 7

A composition as prepared in example 5 was administered subcutaneously to three rabbits (A, B and C) at a dosage unit of 0.1 mg per animal and the same subcutaneous administration was repeated 21 days later. Blood (i.e. antiserum) samples were taken on day 28 after the first administration.

The sera of the immunized rabbits were tested for their potency to neutralize (in vitro, 2 hours at 37° C.) a fixed amount of ST as determined by the infant mice test (A. G. Dean, loc. cit.); for the control, either phosphate buffer with saline or normal serum were employed instead of antiserum.

The results of the seroneutralization test are given in the following Table I wherein PBS means a buffer solution consisting of NaCl 8 g; KCl 0.2 g; Na$_2$HPO$_4$ 1.15 g; KH$_2$PO$_4$ 0.2 g in distilled water up to 800 ml mixed with a solution of 100 mg of MgCl$_2$.6 aq in 100 ml of distilled water and then to a solution of 0.1 g of CaCl$_2$ in 100 ml of distilled water.

values of gw/bw less than 0.09 are the indication of ST neutralization.

each gw/bw value is the average value of 3 determinations, each of them representing gw/bw of a 4 baby mice pool ST volumes refer to a ST solution containing 1.4 mcg of ST-ACF-D grade toxin per ml.

TABLE I

| Scheme | Antiserum dilution | gw/bw |
|---|---|---|
| Control | | |
| 0.5 ml ST + 0.5 ml PBS | — | 0.102 |
| Rabbit A | | |
| 0.5 ml ST + 0.5 ml antiserum | 1/16 | 0.064 |
| | 1/32 | 0.087 |
| | 1/128 | 0.097 |
| Rabbit B | | |
| 0.5 ml ST + 0.5 ml antiserum | ⅛ | 0.059 |
| | ⅛ | 0.100 |
| Rabbit C | | |
| 0.5 ml ST + 0.5 ml antiserum | ⅛ | 0.059 |
| | 1/16 | 0.098 |

The results demonstrate the immunogenicity of the crosslinked ST.

EXAMPLE 8

A composition as prepared in example 5 but with crosslinked toxin as obtained in example 3 (soluble fraction with molecular weight above 10,000) was administered subcutaneously to three rabbits (K, L and M) at a dosage unit of 0.1 mg per animal and the same subcutaneous administration was repeated 21 days later. Blood (i.e. antiserum) samples were taken on day 28 after the first administration and the seroneutralization tests were carried out as in example 7 but using normal serum instead of PBS. The results are reported in Table II and show the immunogenicity of the crosslinked ST in one animal out of three.

TABLE II

| Scheme | Antiserum dilution | gw/bw |
|---|---|---|
| Control | | |
| 0.5 ml ST + 0.5 ml serum | — | 0.129 |
| Rabbit L | | |
| 0.5 ml ST + 0.5 ml antiserum | 1/1 | 0.060 |
| Rabbit K | | |
| 0.5 ml ST + 0.5 ml antiserum | 1/1 | 0.100 |
| Rabbit M | | |
| 0.5 ml ST + 0.5 ml antiserum | 1/1 | 0.111 |

EXAMPLE 9

A composition as prepared in example 5 but with crosslinked toxin as obtained in example 4 (soluble fraction with molecular weight above 14,000) was administered subcutaneously to three rabbits (H, I and J) at a dosage unit of 0.5 mg per animal and the same subcutaneous administration was repeated 21 days later. Blood (i.e. antiserum) samples were taken on day 28 after the first administration and the seroneutralization tests were carried out as in example 7.

The results are given in the following Table III, showing the immunogenicity of crosslinked ST.

TABLE III

| Scheme | Antiserum dilution | gw/bw |
|---|---|---|
| Control | | |
| 0.5 ml ST + 0.5 ml PBS | — | 0.114 |
| Rabbit H | | |
| 0.5 ml ST + 0.5 ml antiserum | 1/1 | 0.078 |
| Rabbit I | | |
| 0.5 ml ST + 0.5 ml antiserum | 1/1 | 0.073 |
| Rabbit J | | |
| 0.5 ml ST + 0.5 ml antiserum | 1/1 | 0.061 |

EXAMPLE 10

A composition as prepared in example 5 was administered subcutaneously to three piglets (20 kg body weight) at a dosage unit of 0.5 mg (Day 0), 0.5 mg (Day 21) and 5 mg (Day 46) for pigs A and B and 0.1 mg (Day 0), 1 mg (Day 21) and 5 mg (Day 46) for piglet C. Blood (i.e. antiserum) samples were taken at day 61 and seroneutralization tests were carried out as described in example 7.

The results are given in the following Table IV and show the immunogenicity of crosslinked ST.

TABLE IV

| Immunization scheme | Antiserum dilution | gw/bw |
|---|---|---|
| Control | | |
| 0.5 ml ST + 0.5 ml PBS | | 0.111 |
| Pig A | 1/32 | 0.054 |
| 0.5 ml ST + 0.5 ml antiserum | 1/64 | 0.062 |
| | 1/28 | 0.920 |
| Pig B | ⅛ | 0.065 |
| 0.5 ml ST + 0.5 ml antiserum | 1/16 | 0.076 |
| | 1/32 | 0.108 |
| Pig C | 1/16 | 0.055 |
| 0.5 ml ST + 0.5 ml antiserum | 1/32 | 0.059 |

TABLE IV-continued

| Immunization scheme | Antiserum dilution | gw/bw |
|---|---|---|
| | 1/64 | 0.095 |

What I claim is:

1. A *E. coli* ST enterotoxin derivative which consists in *E. coli* enterotoxin crosslinked with a dialdehyde, a di-ketone, a carbodiimide, an isocyanate, an epihalohydrin or a difluoride.

2. A composition for immunizing humans or animals against diarrheal disease due to *E. coli* enterotoxin infection which comprises an *E. coli* ST enterotoxin derivative of claim 1, a pharmaceutical or veterinary carrier for intramuscular, subcutaneous or oral administration thereof and a stabilizer therefor.

* * * * *